United States Patent
Govari et al.

(10) Patent No.: US 11,877,953 B2
(45) Date of Patent: Jan. 23, 2024

(54) PHACOEMULSIFICATION APPARATUS

(71) Applicant: JOHNSON & JOHNSON SURGICAL VISION, INC., Irvine, CA (US)

(72) Inventors: Assaf Govari, Haifa (IL); Vadim Gliner, Haifa (IL)

(73) Assignee: JOHNSON & JOHNSON SURGICAL VISION, INC., Irvine, CA (US)

( * ) Notice: Subject to any disclaimer, the term of this patent is extended or adjusted under 35 U.S.C. 154(b) by 810 days.

(21) Appl. No.: 16/727,100

(22) Filed: Dec. 26, 2019

(65) Prior Publication Data

US 2021/0196513 A1    Jul. 1, 2021

(51) Int. Cl.
*A61F 9/007* (2006.01)
*G01R 25/00* (2006.01)
(Continued)

(52) U.S. Cl.
CPC .......... *A61F 9/00745* (2013.01); *A61B 17/32* (2013.01); *A61B 17/320068* (2013.01); *G01R 25/00* (2013.01); *H10N 30/802* (2023.02)

(58) Field of Classification Search
CPC ........... A61B 2017/00017; A61B 2017/00106; A61B 2017/0011; A61B 2017/320073;
(Continued)

(56) References Cited

U.S. PATENT DOCUMENTS 2,434,480 A    1/1948 Anderson
2,763,840 A    9/1956 Pfleger
(Continued)

FOREIGN PATENT DOCUMENTS

CA    2242328 A1    5/1998
CN    109029690 A    12/2018
(Continued)

OTHER PUBLICATIONS

Davis, P.L., et al., "Cavitating Microbubbles Create Shock Waves that Emulsify Cataract," in: The Art of Phacoemulsification, Mehta K.R., et al., eds., Jaypee Brothers,New Delhi, 2001, pp. 45-50.
(Continued)

*Primary Examiner* — Kathleen S Holwerda
(74) *Attorney, Agent, or Firm* — Johnson & Johnson Surgical Vision, Inc.

(57) ABSTRACT

In one embodiments, a phacoemulsification apparatus includes a phacoemulsification probe including a horn, a needle mounted in the horn and configured for insertion into a lens capsule of a human eye, and a piezoelectric actuator configured to vibrate the horn and the needle and having a resonant frequency, a signal generator configured to generate a drive signal to drive a vibration of the piezoelectric actuator, phase detection circuitry configured to measure a phase difference between: a voltage across the piezoelectric actuator, and a current flowing through the piezoelectric actuator in response to the drive signal, and a controller configured to adjust a frequency of the drive signal so as to minimize the measured phase difference, whereby the piezoelectric actuator vibrates at the resonant frequency.

19 Claims, 8 Drawing Sheets

(51) Int. Cl.
*A61B 17/32* (2006.01)
*H10N 30/80* (2023.01)

(58) Field of Classification Search
CPC ....... A61B 2017/320074; A61B 2017/320082;
A61B 2017/320098; A61B 17/22004;
A61B 17/320068; A61F 9/00745; H01L
41/042; G01R 25/00; B06B 1/0253
See application file for complete search history.

(56) References Cited

U.S. PATENT DOCUMENTS

| | | |
|---|---|---|
| 3,469,213 A | 9/1969 | Leonard |
| 3,857,387 A | 12/1974 | Shock |
| 3,885,569 A | 5/1975 | Judson |
| 3,941,122 A | 3/1976 | Jones |
| 4,012,647 A | 3/1977 | Balamuth et al. |
| 4,063,557 A | 12/1977 | Wuchinich et al. |
| 4,092,986 A | 6/1978 | Schneiderman |
| 4,156,187 A | 5/1979 | Brumbach et al. |
| 4,184,510 A | 1/1980 | Murry et al. |
| 4,199,246 A | 4/1980 | Muggli |
| 4,343,111 A | 8/1982 | Inoue |
| 4,378,538 A | 3/1983 | Gignoux |
| 4,469,098 A | 9/1984 | Davi |
| 4,520,818 A | 6/1985 | Mickiewicz |
| 4,736,130 A | 4/1988 | Puskas |
| 4,808,948 A | 2/1989 | Patel et al. |
| 4,827,911 A | 5/1989 | Broadwin et al. |
| 4,861,332 A | 8/1989 | Parisi |
| 4,886,060 A | 12/1989 | Wiksell |
| 4,903,696 A | 2/1990 | Stasz et al. |
| 4,952,834 A | 8/1990 | Okada |
| 4,954,960 A * | 9/1990 | Lo ..................... B06B 1/0253 331/181 |
| 4,970,656 A | 11/1990 | Lo et al. |
| 4,983,901 A | 1/1991 | Lehmer |
| 5,001,649 A | 3/1991 | Lo et al. |
| 5,019,794 A | 5/1991 | Lei et al. |
| 5,091,656 A | 2/1992 | Gahn |
| 5,162,044 A | 11/1992 | Gahn et al. |
| 5,162,759 A | 11/1992 | Yajima |
| 5,209,221 A | 5/1993 | Riedlinger |
| 5,213,569 A | 5/1993 | Davis |
| 5,242,404 A | 9/1993 | Conley et al. |
| 5,249,121 A | 9/1993 | Baum et al. |
| 5,268,624 A | 12/1993 | Zanger |
| 5,279,547 A | 1/1994 | Costin |
| 5,318,563 A | 6/1994 | Malis et al. |
| 5,331,951 A | 7/1994 | Kepley |
| 5,342,293 A | 8/1994 | Zanger |
| 5,370,602 A | 12/1994 | Kepley |
| 5,388,569 A | 2/1995 | Kepley |
| 5,403,307 A | 4/1995 | Zelman |
| 5,405,614 A | 4/1995 | D'Angelo et al. |
| 5,406,503 A | 4/1995 | Williams, Jr. et al. |
| 5,417,246 A | 5/1995 | Perkins et al. |
| 5,431,663 A | 7/1995 | Carter |
| 5,431,664 A | 7/1995 | Ureche et al. |
| 5,451,161 A | 9/1995 | Sharp |
| 5,453,087 A | 9/1995 | Malinowski |
| 5,520,633 A | 5/1996 | Costin |
| 5,523,058 A | 6/1996 | Umemura et al. |
| 5,534,741 A | 7/1996 | Smith |
| 5,547,459 A | 8/1996 | Kaufman et al. |
| 5,549,632 A | 8/1996 | Lai |
| 5,582,578 A | 12/1996 | Zhong et al. |
| 5,591,127 A | 1/1997 | Barwick, Jr. et al. |
| 5,700,240 A | 12/1997 | Barwick, Jr. et al. |
| 5,733,256 A | 3/1998 | Costin |
| 5,738,677 A | 4/1998 | Colvard et al. |
| 5,766,146 A | 6/1998 | Barwick, Jr. |
| 5,797,494 A | 8/1998 | Balling et al. |
| 5,800,365 A | 9/1998 | Zhong et al. |
| 5,808,396 A | 9/1998 | Boukhny |
| 5,825,164 A | 10/1998 | Williams et al. |
| 5,836,959 A | 11/1998 | Seibel et al. |
| 5,843,109 A | 12/1998 | Mehta et al. |
| 5,852,794 A | 12/1998 | Staggs |
| 5,873,885 A | 2/1999 | Weidenbenner |
| 5,897,569 A | 4/1999 | Kellogg et al. |
| 5,938,677 A | 8/1999 | Boukhny et al. |
| 5,971,980 A | 10/1999 | Sherman |
| 5,979,494 A | 11/1999 | Perkins et al. |
| 5,984,882 A | 11/1999 | Rosenschein et al. |
| 5,997,528 A | 12/1999 | Bisch et al. |
| 6,010,496 A | 1/2000 | Appelbaum et al. |
| 6,027,515 A | 2/2000 | Cimino |
| 6,028,387 A | 2/2000 | Boukhny |
| 6,053,906 A * | 4/2000 | Honda .................. B06B 1/0253 606/1 |
| 6,083,193 A | 7/2000 | Kadziauskas et al. |
| 6,086,598 A | 7/2000 | Appelbaum et al. |
| 6,117,126 A | 9/2000 | Appelbaum et al. |
| 6,155,975 A | 12/2000 | Urich et al. |
| 6,161,545 A | 12/2000 | Chow |
| 6,174,309 B1 | 1/2001 | Wrublewski et al. |
| 6,175,180 B1 | 1/2001 | Angelini et al. |
| 6,193,683 B1 | 2/2001 | Ludin et al. |
| 6,203,516 B1 | 3/2001 | Kepley |
| 6,251,113 B1 | 6/2001 | Appelbaum et al. |
| 6,261,297 B1 | 7/2001 | Kadziauskas et al. |
| 6,319,220 B1 | 11/2001 | Bylsma |
| 6,391,020 B1 | 5/2002 | Kurtz et al. |
| 6,391,042 B1 | 5/2002 | Cimino |
| 6,394,974 B1 | 5/2002 | Kadziauskas et al. |
| 6,402,769 B1 | 6/2002 | Boukhny |
| 6,425,883 B1 | 7/2002 | Urich et al. |
| 6,428,531 B1 | 8/2002 | Visuri et al. |
| 6,443,900 B2 | 9/2002 | Adachi et al. |
| 6,452,120 B1 | 9/2002 | Chen |
| 6,452,123 B1 | 9/2002 | Chen |
| 6,452,883 B2 | 9/2002 | Chan |
| 6,487,447 B1 | 11/2002 | Weimann et al. |
| 6,506,176 B1 | 1/2003 | Mittelstein et al. |
| 6,588,277 B2 | 7/2003 | Giordano et al. |
| 6,589,204 B1 | 7/2003 | Sussman et al. |
| 6,610,052 B2 | 8/2003 | Furumoto |
| 6,629,948 B2 | 10/2003 | Rockley et al. |
| 6,632,193 B1 | 10/2003 | Davison et al. |
| 6,699,212 B1 | 3/2004 | Kadziauskas et al. |
| 6,726,679 B1 | 4/2004 | Dick et al. |
| 6,733,491 B2 | 5/2004 | Kadziauskas et al. |
| 6,780,165 B2 | 8/2004 | Kadziauskas et al. |
| 6,808,396 B2 | 10/2004 | Kawaguchi et al. |
| 6,884,252 B1 | 4/2005 | Urich et al. |
| 6,890,332 B2 | 5/2005 | Truckai et al. |
| 6,896,674 B1 | 5/2005 | Woloszko et al. |
| 6,908,472 B2 | 6/2005 | Wiener et al. |
| 6,939,317 B2 | 9/2005 | Zacharias |
| 6,945,981 B2 | 9/2005 | Donofrio et al. |
| 6,962,583 B2 | 11/2005 | Kadziauskas et al. |
| 6,997,935 B2 | 2/2006 | Anderson et al. |
| 7,077,820 B1 | 7/2006 | Kadziauskas et al. |
| 7,169,123 B2 | 1/2007 | Kadziauskas et al. |
| 7,193,521 B2 | 3/2007 | Moberg et al. |
| 7,316,664 B2 | 1/2008 | Kadziauskas et al. |
| 7,485,106 B2 | 2/2009 | Kadziauskas et al. |
| 7,671,693 B2 | 3/2010 | Brobston et al. |
| 7,785,336 B2 | 8/2010 | Staggs |
| 7,857,783 B2 | 12/2010 | Kadziauskas et al. |
| 7,938,120 B2 | 5/2011 | Kadziauskas et al. |
| 7,998,156 B2 | 8/2011 | Staggs |
| 8,020,565 B2 | 9/2011 | Kadziauskas et al. |
| 8,034,067 B2 | 10/2011 | Staggs |
| 8,195,286 B2 | 6/2012 | Kadziauskas et al. |
| 8,197,436 B2 | 6/2012 | Kadziauskas et al. |
| 8,202,287 B2 | 6/2012 | Staggs |
| 8,231,564 B2 | 7/2012 | Kadziauskas et al. |
| 8,303,613 B2 | 11/2012 | Crandall et al. |
| 8,366,728 B2 | 2/2013 | Staggs |
| 8,545,528 B2 | 10/2013 | Rob et al. |
| 8,623,040 B2 | 1/2014 | Artsyukhovich et al. |
| 8,852,138 B2 | 10/2014 | Kadzlauskas et al. |

(56) References Cited

U.S. PATENT DOCUMENTS

| | | |
|---|---|---|
| 8,876,747 B2 | 11/2014 | Kadziauskas et al. |
| 8,887,735 B2 | 11/2014 | Kadzlauskas et al. |
| 8,945,162 B2 | 2/2015 | Kadziauskas et al. |
| 9,018,887 B2 | 4/2015 | Paschke |
| 9,226,849 B2 | 1/2016 | Staggs |
| 9,572,711 B2 | 2/2017 | Raney et al. |
| 9,642,745 B2 | 5/2017 | Kadziauskas et al. |
| 9,707,127 B2 | 7/2017 | Kadziauskas |
| 9,788,998 B2 | 10/2017 | Kadziauskas et al. |
| 10,245,179 B2 | 4/2019 | Kadziauskas et al. |
| 10,478,337 B2 | 11/2019 | Greenbaum et al. |
| 2001/0003155 A1 | 6/2001 | Rockley et al. |
| 2001/0003295 A1 | 6/2001 | Langlotz et al. |
| 2001/0003385 A1 | 6/2001 | Ise |
| 2001/0039389 A1* | 11/2001 | Sakurai ............... B06B 1/0253 601/2 |
| 2001/0048356 A1 | 12/2001 | Owen et al. |
| 2002/0010477 A1 | 1/2002 | Hirt et al. |
| 2002/0052600 A1 | 5/2002 | Davison et al. |
| 2002/0072741 A1 | 6/2002 | Sliwa et al. |
| 2002/0082793 A1 | 6/2002 | Kadziauskas et al. |
| 2002/0173814 A1 | 11/2002 | Jung et al. |
| 2003/0047434 A1 | 3/2003 | Hanson et al. |
| 2004/0092921 A1 | 5/2004 | Kadziauskas et al. |
| 2004/0092922 A1 | 5/2004 | Kadziauskas et al. |
| 2004/0193182 A1 | 9/2004 | Yaguchi et al. |
| 2005/0054971 A1 | 3/2005 | Steen et al. |
| 2005/0209560 A1 | 9/2005 | Boukhny et al. |
| 2005/0209621 A1 | 9/2005 | Gordon et al. |
| 2005/0288665 A1 | 12/2005 | Woloszko |
| 2006/0036180 A1* | 2/2006 | Boukhny ............ A61F 9/00745 600/471 |
| 2006/0079788 A1 | 4/2006 | Anderson et al. |
| 2006/0149301 A1 | 7/2006 | Claus |
| 2006/0195077 A1 | 8/2006 | Kadziauskas et al. |
| 2006/0264809 A1 | 11/2006 | Hansmann et al. |
| 2007/0056596 A1 | 3/2007 | Fanney et al. |
| 2007/0066978 A1 | 3/2007 | Schafer et al. |
| 2007/0073214 A1 | 3/2007 | Dacquay et al. |
| 2007/0078379 A1 | 4/2007 | Boukhny et al. |
| 2007/0249941 A1 | 10/2007 | Salehi et al. |
| 2008/0139994 A1 | 6/2008 | Mackool et al. |
| 2008/0146989 A1 | 6/2008 | Zacharias |
| 2008/0154255 A1 | 6/2008 | Panos et al. |
| 2008/0294087 A1 | 11/2008 | Steen et al. |
| 2008/0319374 A1 | 12/2008 | Zacharias |
| 2009/0005712 A1* | 1/2009 | Raney ............... A61F 9/00745 601/2 |
| 2010/0069825 A1 | 3/2010 | Raney |
| 2010/0125292 A1* | 5/2010 | Wiener ............ A61B 17/320068 606/169 |
| 2010/0185150 A1 | 7/2010 | Zacharias |
| 2011/0196403 A1 | 8/2011 | Robertson et al. |
| 2011/0196404 A1 | 8/2011 | Dietz et al. |
| 2012/0029353 A1 | 2/2012 | Slayton |
| 2013/0006265 A1 | 1/2013 | Crandall et al. |
| 2013/0057253 A1 | 3/2013 | Jacobson |
| 2013/0314077 A1 | 11/2013 | Okada et al. |
| 2013/0331872 A1 | 12/2013 | Parham et al. |
| 2014/0024969 A1 | 1/2014 | Govari et al. |
| 2014/0074013 A1 | 3/2014 | Mccary et al. |
| 2015/0148712 A1 | 5/2015 | Loven |
| 2017/0312129 A1 | 11/2017 | Kadziauskas et al. |
| 2018/0056328 A1 | 3/2018 | Downey et al. |
| 2021/0330493 A1 | 10/2021 | Steen et al. |
| 2021/0361481 A1 | 11/2021 | Gliner et al. |
| 2022/0096269 A1 | 3/2022 | Gliner et al. |

FOREIGN PATENT DOCUMENTS

| | | |
|---|---|---|
| DE | 232755 A1 | 2/1986 |
| DE | 3910200 A1 | 10/1990 |
| DE | 19940712 A1 | 3/2001 |
| EP | 270819 A2 | 6/1988 |
| EP | 270819 A3 | 1/1989 |
| EP | 336620 A2 | 10/1989 |
| EP | 336620 B1 | 12/1993 |
| EP | 0945732 A2 | 9/1999 |
| EP | 1351631 A1 | 10/2003 |
| EP | 0955984 B1 | 4/2004 |
| EP | 1537840 A1 | 6/2005 |
| EP | 1608280 A2 | 12/2005 |
| EP | 1625836 A1 | 2/2006 |
| EP | 1849444 A1 | 10/2007 |
| JP | 63315049 A | 12/1988 |
| JP | 2204337 A2 | 8/1990 |
| JP | 5038343 A2 | 2/1993 |
| JP | 6183762 A2 | 7/1994 |
| JP | 6189972 A2 | 7/1994 |
| JP | 9313496 A2 | 12/1997 |
| JP | 2001161740 A2 | 6/2001 |
| JP | 2002087836 A2 | 3/2002 |
| JP | 2002233534 A2 | 8/2002 |
| WO | 9211814 A1 | 7/1992 |
| WO | 9520374 A1 | 8/1995 |
| WO | 9808442 A1 | 3/1998 |
| WO | 0000298 A1 | 1/2000 |
| WO | 0051508 A1 | 9/2000 |
| WO | 0064388 A1 | 11/2000 |
| WO | 0113838 A1 | 3/2001 |
| WO | 0152782 A1 | 7/2001 |
| WO | 02056806 A1 | 7/2002 |
| WO | 05092023 A2 | 10/2005 |
| WO | 2013173495 A1 | 11/2013 |
| WO | WO2018022968 A1 | 2/2018 |

OTHER PUBLICATIONS

Devine M.T., ed., "How to Set the Dials," in: Phacoemulsification Surgery, Pergamon Press, Chapter 2, 1991, pp. 7-28.

Ocusystem Operation Manual, May 1995, 79 pages.

Ophthalmology Times, Pulsar Cuts Phaco Time, Boosts Efficiency in Cataract Removal, Aug. 15, 1986, vol. 11 (16), Harcourt Brace Jovanovich, Inc., 1 page.

Pacifico R.L., "Ultrasonic Energy in Phacoemulsification: Mechanical Cutting and Cavitation," Journal of Cataract & Refractive Surgery, 1994, vol. 20 (3), pp. 338-341.

Taylor W.F., et al., "Intraoperative Troubleshooting of an Advanced Phacoemulsification System," The Surgial Technologist, 1985, vol. 17 (2), pp. 11-14.

U.S. Appl. No. 16/704,054, filed Dec. 5, 2019, titled "Phacoemulsification Apparatus".

Co-Pending U.S. Appl. No. 17/231,450, filed Apr. 15, 2021, 20 pages.

* cited by examiner

PHACOEMULSIFICATION APPARATUS

FIELD OF THE INVENTION

The present invention relates to medical systems, and in particular, but not exclusively to, a phacoemulsification apparatus and associated method.

BACKGROUND

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this a physician may recommend phacoemulsification cataract surgery. Before the procedure the surgeon numbs the area with anesthesia. Pressure may also be applied to increase the internal pressure within the eye. This lowers the chances of complications later in the surgery. Then a small incision is made in the cornea of the eye. Fluids are injected into this incision to support the surrounding structures. The anterior surface of the lens capsule is then removed to gain access to the cataract. The surgeon then uses a phacoemulsification probe, which has an ultrasonic handpiece with a titanium or steel needle. The tip of the needle vibrates at ultrasonic frequency to sculpt and emulsify the cataract while a pump aspirates particles from the cataract through the tip. The pump is typically controlled with a microprocessor. The pump may be a peristaltic or a venturi type of pump. Aspirated fluids are replaced with irrigation of a balanced salt solution to maintain the anterior chamber of the eye. After removing the cataract with phacoemulsification, the softer outer lens cortex is removed with suction. An Intraocular Lens (IOL) is introduced with the phacoemulsification probe through its needle into the empty lens capsule and the IOL unfolds. Small struts may hold the IOL in place. Once correctly installed the IOL restores the patient's vision.

US Patent Publication 2015/0148712 to Loven, et al., describes non-contact, medical ultrasound therapy system for generating and controlling low frequency ultrasound. The ultrasound therapy system includes a treatment wand including an ultrasonic transducer, a generator unit, and a cable coupling the treatment wand to the generator unit. The generator unit generates electric power output to drive the ultrasonic transducer and includes a digital frequency generator, wherein the generator unit digitally controls energy output at the resonance frequency of the ultrasonic transducer.

US Patent Publication 2012/0029353 to Slayton, et al., describes a method for an extended field of view treatment. The method can include the steps of imaging a region; targeting a region with directed ultrasound energy; monitoring the region; moving the imaging, treatment, and monitoring region while spatially correlating to one or more prior regions via imaging and/or position sensing; continuing the extended field of view treatment; and, achieving an ultrasound induced biological effect in the extended field of view treatment region.

US Patent Publication 2009/0005712 to Raney describes a method and system for controlling an ultrasonically driven handpiece employable in an ocular surgical procedure. The method includes operating the ultrasonically driven handpiece in a first tip displacement mode, such as a longitudinal mode according to a first set of operational parameters, and enabling a user to alter the ultrasonically driven handpiece to employ a second tip displacement mode, Such as a transversal or torsional mode, using a second set of operational parameters. Enabling the user to alter performance of the handpiece comprises the user being enabled to dynamically select operational parameters for the first tip displacement mode relative to the second tip displacement mode by using, for example, a Switching apparatus such as a foot pedal.

SUMMARY

There is provided in accordance with an exemplary embodiment of the present invention, a phacoemulsification apparatus including a phacoemulsification probe including a horn, a needle mounted in the horn and configured for insertion into a lens capsule of a human eye, and a piezoelectric actuator configured to vibrate the horn and the needle and having a resonant frequency, a signal generator configured to generate a drive signal to drive a vibration of the piezoelectric actuator, phase detection circuitry configured to measure a phase difference between a voltage across the piezoelectric actuator, and a current flowing through the piezoelectric actuator in response to the drive signal, and a controller configured to adjust a frequency of the drive signal so as to minimize the measured phase difference, whereby the piezoelectric actuator vibrates at the resonant frequency.

Further in accordance with an exemplary embodiment of the present invention, the phase detection circuitry includes a first analog multiplier configured to perform a multiplication of the voltage with a reference signal yielding voltage resultant signals, and a second analog multiplier configured to perform a multiplication of the current with the reference signal yielding current resultant signals.

Still further in accordance with an exemplary embodiment of the present invention, the phase detection circuitry also includes a first analog-to-digital convertor configured to sample the voltage resultant signals yielding voltage resultant signal samples, a second analog-to-digital convertor configured to sample the current resultant signals yielding current resultant signal samples, and a phase computation processor configured to compute the phase difference responsively to the voltage resultant signal samples and the current resultant signal samples.

Additionally, in accordance with an exemplary embodiment of the present invention, the apparatus includes a connection in series with the piezoelectric actuator, and a resister disposed in the connection, wherein the second analog multiplier has inputs connected across the resister.

Moreover, in accordance with an exemplary embodiment of the present invention, the reference signal includes the drive signal.

Further in accordance with an exemplary embodiment of the present invention, the phase detection circuitry includes analog multipliers configured to perform a multiplication of the voltage with the current yielding resultant signals, analog-to-digital convertors configured to sample the resultant signals yielding resultant signal samples, and a phase computation processor configured to compute the phase difference responsively to the resultant signal samples.

Still further in accordance with an exemplary embodiment of the present invention, the controller is configured adjust the frequency of the drive signal so as to minimize the measured phase difference based on an optimization algorithm.

Additionally, in accordance with an exemplary embodiment of the present invention, the optimization algorithm includes a gradient descent algorithm.

Moreover, in accordance with an exemplary embodiment of the present invention, the signal generator includes a direct digital synthesizer (DDS) and a class AB amplifier, the DDS being configured to generate the drive signal, the class AB amplifier being configured to amplify the drive signal to power the piezoelectric actuator.

Further in accordance with an exemplary embodiment of the present invention, the piezoelectric actuator includes two different resonance modes having two respective resonant frequencies, the controller being configured to adjust the frequency of the drive signal so as to minimize the measured phase difference, whereby the piezoelectric actuator vibrates at a respective one of the resonant frequencies of a respective selected one of the resonance modes.

Still further in accordance with an exemplary embodiment of the present invention, the resonance modes include a longitudinal resonance mode and a transverse or torsion resonance mode.

There is also provided in accordance with another exemplary embodiment of the present invention, a phacoemulsification method including inserting a needle of a phacoemulsification probe into a lens capsule of a human eye, the probe also including a horn in which the needle is mounted, generating a drive signal to drive a vibration of a piezoelectric actuator having a resonant frequency, the piezoelectric actuator vibrating the horn and the needle, measuring a phase difference between a voltage across the piezoelectric actuator, and a current flowing through the piezoelectric actuator in response to the drive signal, and adjusting a frequency of the drive signal so as to minimize the measured phase difference, whereby the piezoelectric actuator vibrates at the resonant frequency.

Additionally, in accordance with exemplary embodiment of the present invention, the method includes performing a multiplication of the voltage with a reference signal yielding voltage resultant signals, and performing a multiplication of the current with the reference signal yielding current resultant signals.

Moreover, in accordance with an exemplary embodiment of the present invention, the method includes sampling the voltage resultant signal yielding voltage resultant signal samples, sampling the current resultant signal yielding current resultant signal samples, and computing the phase difference responsively to the voltage resultant signal samples and the current resultant signal samples.

Further in accordance with an exemplary embodiment of the present invention, the reference signal includes the drive signal.

The method further including performing a multiplication of the voltage with the current yielding resultant signals, sampling the resultant signals yielding resultant signal samples, and computing the phase difference responsively to the resultant signal samples.

Still further in accordance with an exemplary embodiment of the present invention, the adjusting includes adjusting the frequency of the drive signal so as to minimize the measured phase difference based on an optimization algorithm.

Additionally, in accordance with an exemplary embodiment of the present invention, the optimization algorithm includes a gradient descent algorithm.

Moreover, in accordance with an exemplary embodiment of the present invention, the method includes amplifying the drive signal to power the piezoelectric actuator.

Further in accordance with an exemplary embodiment of the present invention, the piezoelectric actuator includes two different resonance modes having two respective resonant frequencies, wherein the adjusting includes adjusting the frequency of the drive signal so as to minimize the measured phase difference, whereby the piezoelectric actuator vibrates at a respective one of the resonant frequencies of a respective selected one of the resonance modes.

Still further in accordance with an exemplary embodiment of the present invention, the resonance modes include a longitudinal resonance mode and a transverse or torsion resonance mode.

BRIEF DESCRIPTION OF THE DRAWINGS

The foregoing and other features and advantages of the invention will be apparent from the following, more particular description of preferred embodiments of the invention, as illustrated in the accompanying drawings.

DESCRIPTION OF EXAMPLE EMBODIMENTS

Overview

A phacoemulsification probe typically includes a piezoelectric actuator to drive a needle of the phacoemulsification probe during a cataract procedure. The stroke amplitude of the needle is not only a function of the voltage applied to the piezoelectric actuator of the probe, but is generally at a maximum when the piezoelectric actuator is operating at its resonant frequency. When the piezoelectric actuator is not operating at its resonant frequency, the stoke amplitude is less than the maximum and the electrical energy used to power the piezoelectric actuator is converted to heat thereby heating the phacoemulsification probe.

The resonant frequency may depend on the geometry of the rest of the probe and other factors such as temperature of the piezoelectric actuator, the voltage and current amplitude applied to the piezoelectric actuator, and acoustic impedance encountered by the piezoelectric actuator.

For example, the resonant frequency of the piezoelectric actuator may change when a load is applied to the needle. Therefore, when the needle is outside the eye, the resonant frequency is at one value, and when the needle is inserted into the eye, the resonant frequency changes to another value, and when the needle is impacting a cataract, the resonant frequency changes to yet another value. As previously mentioned, another factor that affects the resonant frequency of the piezoelectric actuator is temperature. So, for example, if the resonant frequency of the piezoelectric actuator changes due to the needle impacting a cataract, and the piezoelectric actuator is still powered with the same frequency signal, the piezoelectric actuator will start to heat and the stoke amplitude will decrease. The additional heat will lead to further changes in the resonant frequency, which in turn leads to further heat and even less stroke amplitude, and so on.

The resonant frequency of the piezoelectric actuator is non-linear and inadequate control can lead to the phacoemulsification probe providing an inadequate needle stroke amplitude and becoming too hot for the eye. For example, the phacoemulsification probe could reach a temperature of 42 degrees, above which the proteins in the eye could coagulate, which is potentially very dangerous for the eye.

Therefore, irrigation is used to reduce the temperature of the phacoemulsification probe. However, irrigation has its own problems as irrigation without carefully matched aspiration can lead to too much pressure in the eye, which is also potentially dangerous, whereas too much aspiration can lead to the eye collapsing. Moreover, irrigation may not be sufficient to adequately cool the phacoemulsification probe.

Exemplary embodiments of the present invention solve the above problems by providing a phacoemulsification apparatus that dynamically adjusts a frequency of a drive signal to drive a piezoelectric actuator of a phacoemulsification probe to follow the resonant frequency of the piezoelectric actuator thereby maximizing stroke amplitude while minimizing temperature rise of the phacoemulsification probe. The frequency of the drive signal is adjusted to minimize a measured phase difference between a voltage across the piezoelectric actuator and a current flowing through the piezoelectric actuator in response to the drive signal, thereby causing the piezoelectric actuator to vibrate at the resonant frequency.

In some exemplary embodiments, the phacoemulsification apparatus comprises the phacoemulsification probe including a horn, a needle mounted in the horn for insertion into a lens capsule of a human eye, and the piezoelectric actuator vibrating the horn and the needle. The apparatus also includes a signal generator which generates a drive signal to drive a vibration of the piezoelectric actuator, phase detection circuitry which measures the phase difference between the voltage across the piezoelectric actuator and the current flowing through the piezoelectric actuator in response to the drive signal, and a controller (e.g., microcontroller or any suitable processor) to adjust the frequency of the drive signal so as to minimize the measured phase difference, whereby the piezoelectric actuator vibrates at the resonant frequency.

The controller may adjust the frequency of the drive signal to minimize the measured phase difference using any suitable method, for example, using an optimization algorithm, for example, but not limited to, a gradient descent algorithm.

In some exemplary embodiments, the phase difference may be measured using respective analog-to-digital converters which sample the voltage across, and the current through, the piezoelectric actuator, with the output of the analog-to-digital converters being digitally analyzed to compute the phase difference. Use of some analog-to-digital converters is limited by their sampling rate and therefore sampling the voltage and current directly using the analog-to-digital converters may be unsuitable for some drive frequencies of the piezoelectric actuator (e.g., above 40 kHz). Although other high-end analog-to-digital convertors may provide a high enough sampling rate even for drive frequencies up to 250 kHz, these analog-to-digital convertors may be expensive and large and result in too much output data to be processed efficiently.

In some exemplary embodiments, the phase difference may be measured using the output of analog multipliers as described below. The phase detection circuitry performs a multiplication of the voltage (across the piezoelectric actuator) with a given reference signal (such as the drive signal) and a multiplication of the voltage with a quadrature reference signal (which is in quadrature (i.e., 90 degrees out-of-phase) with the given reference signal, which is also referred to as the in-phase reference signal) yielding two respective direct current (DC) voltage resultant signals, an in-phase resultant signal (based on the in-phase reference signal) and a quadrature resultant signal (based on the quadrature reference signal), respectively. The phase detection circuitry performs a multiplication of the current (flowing through the piezoelectric actuator) with the reference signal and a multiplication of the current with the quadrature reference signal yielding two respective DC current resultant signals, an in-phase resultant signal (based on the in-phase reference signal) and a quadrature resultant signal (based on the quadrature reference signal), respectively. Respective analog-to-digital convertors sample the respective voltage and current resultant signals yielding respective voltage resultant signal samples (in-phase resultant signal samples and quadrature resultant signal samples) and respective current resultant signal samples (in-phase resultant signal samples and quadrature resultant signal samples). A phase computation processor computes respective phase differences responsively to the respective voltage resultant signal samples and the respective current resultant signal samples. For example, the phase computation processor computes the phase difference between the voltage across the piezoelectric actuator and the reference signal at time t by computing a first arctan of: (a) the quadrature voltage resultant signal sample at time t divided; by (b) the in-phase voltage resultant signal sample at time t. Similarly, the phase computation processor computes the phase difference between the current flowing through the piezoelectric actuator and the reference signal at time t by computing a second arctan of: (a) the quadrature current resultant signal sample at time t divided by; (b) the in-phase current resultant signal sample at time t. The phase computation processor computes the phase difference between the voltage and the current at time t, by subtracting the result of the first arctan from the second arctan, or vice-versa.

In some exemplary embodiments, the phase difference may be computed based on multiplying the voltage (across the piezoelectric actuator) signal with the current (flowing through the piezoelectric actuator) signal and multiplying the voltage signal with a signal in quadrature with the current signal yielding an in-phase resultant signal and a quadrature resultant signal, respectively. The multiplied outputs are sampled and the phase computation processor computes the phase difference between the voltage and the current at time t by computing an arctan of: (a) the quadrature resultant signal sample at time t, divided by; (b) the in-phase current resultant signal sample at time t.

The phase computation processor may be implemented as part of the functionality of the controller.

In some exemplary embodiments, the signal generator may include a direct digital synthesizer (DDS) which generates the drive signal and a class AB amplifier which amplifies the drive signal to power the piezoelectric actuator.

In some exemplary embodiments, the piezoelectric actuator may include two (or more) different resonance modes having two (or more) respective resonant frequencies. The resonance modes may include a longitudinal resonance mode and a transverse or torsion resonance mode, by way of example. The controller adjusts the frequency of the drive signal so as to minimize the measured phase difference, whereby the piezoelectric actuator vibrates at a respective one of the resonant frequencies of a respective selected one of the resonance modes.

SYSTEM DESCRIPTION

Figure 1:
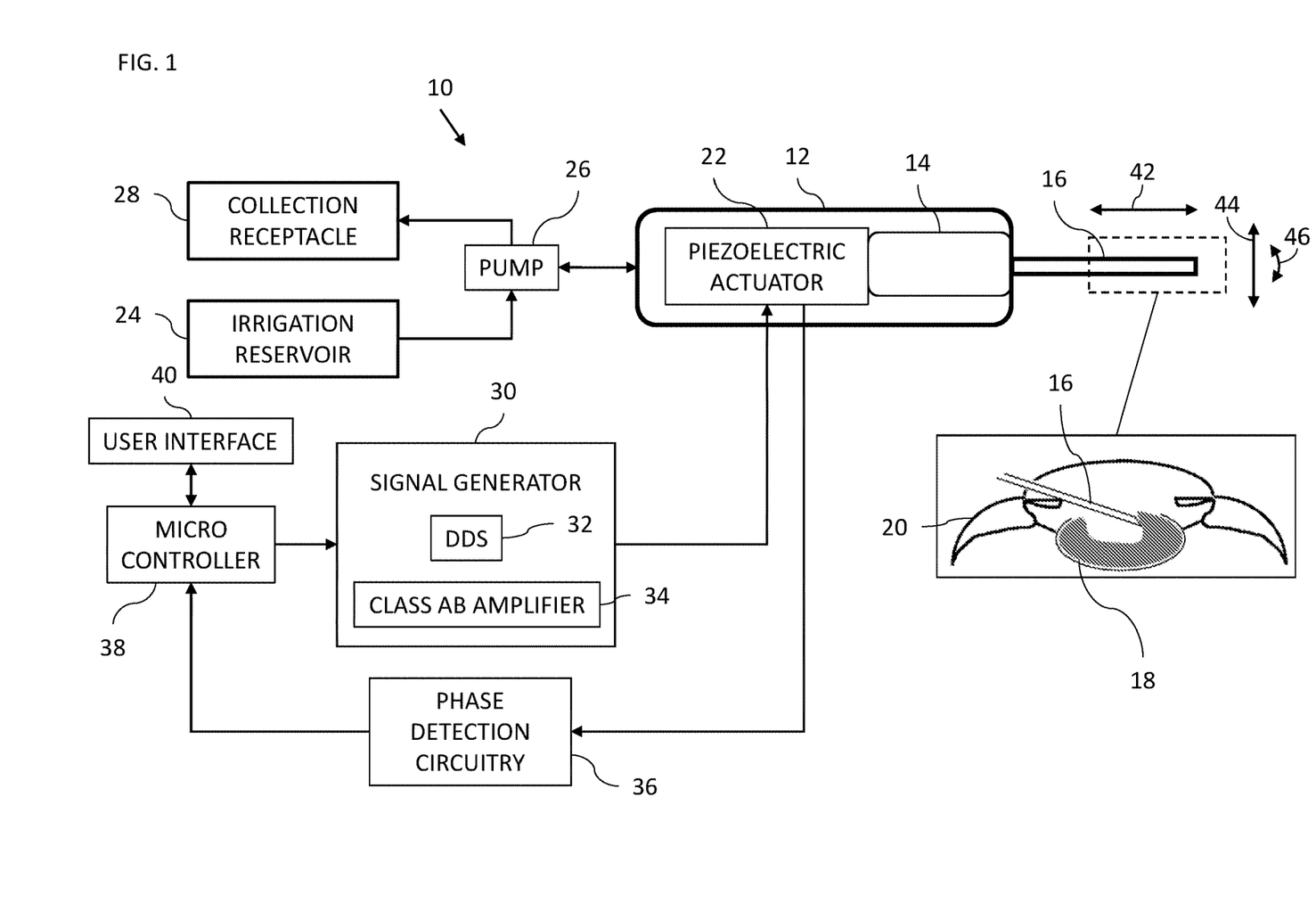
FIG. 1 is a partly pictorial, partly block diagram view of a phacoemulsification apparatus constructed and operative in accordance with an exemplary embodiment of the present invention.
Figure 2:
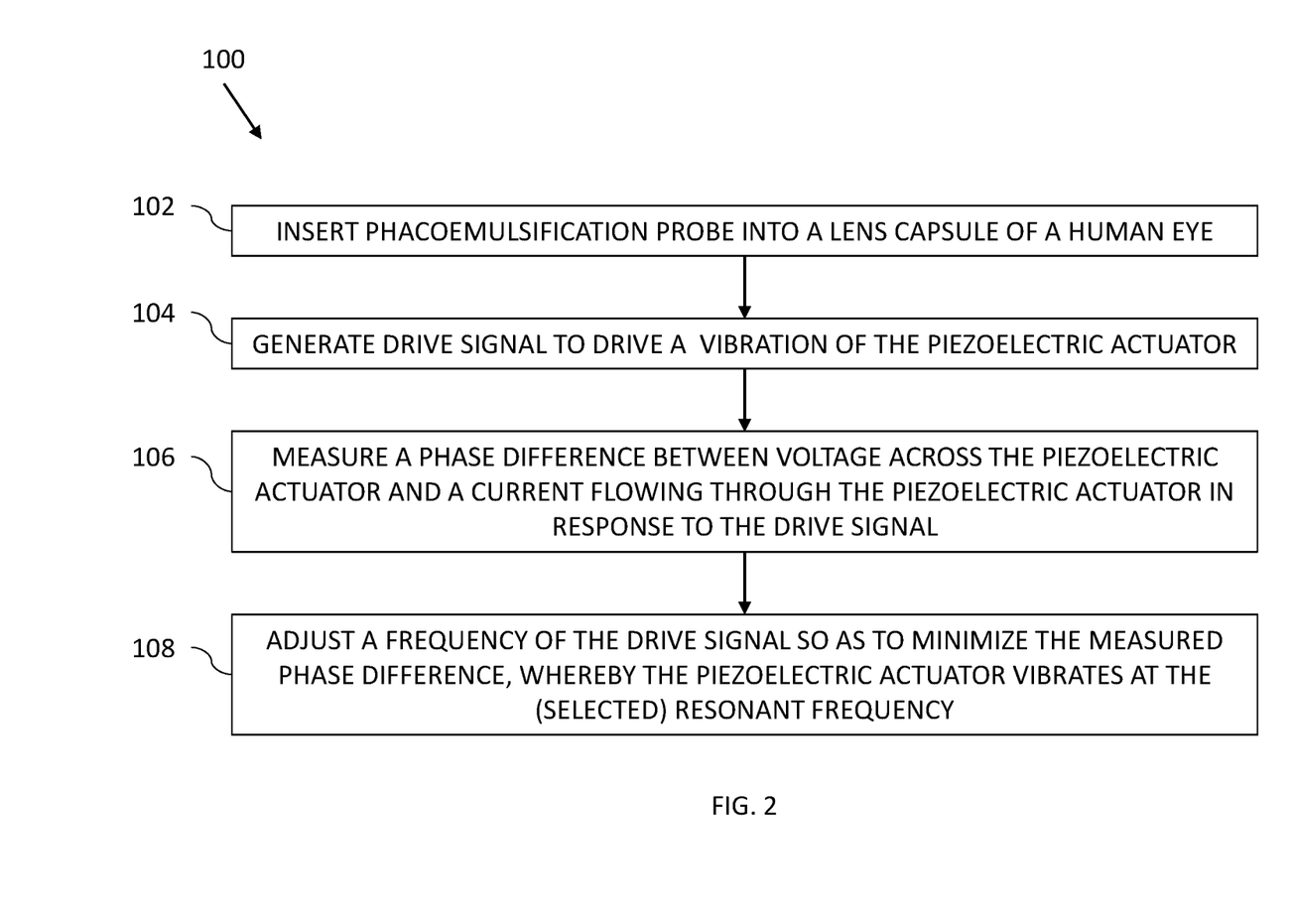
FIG. 2 is a flowchart including steps of a method of operation of the apparatus of FIG. 1 in accordance with an exemplary embodiment of the present invention.

Reference is now made to FIG. 1, which is a partly pictorial, partly block diagram view of a phacoemulsification apparatus 10 constructed and operative in accordance with an exemplary embodiment of the present invention. Reference is also made to FIG. 2, which is a flowchart 100 including steps of a method of operation of the apparatus 10 of FIG. 1.

The phacoemulsification apparatus 10 includes a phacoemulsification probe 12 including a horn 14, a needle 16 mounted in the horn 14 and configured for insertion (block 102) into a lens capsule 18 of a human eye 20, and a piezoelectric actuator 22 configured to vibrate the horn 14 and the needle 16 and having a resonant frequency associated with a resonance mode. The vibration of the needle 16 is used to break the cataract into small pieces during the phacoemulsification procedure.

The phacoemulsification probe 12 is connected to an irrigation reservoir 24 via a pumping sub-system 26 and to a collection receptacle 28 via the pumping sub-system 26. Irrigation fluid is pumped from the irrigation reservoir 24 by the pumping sub-system 26 to a distal end of the phacoemulsification probe 12 for irrigating the eye during the phacoemulsification procedure. Waste matter (e.g., emulsified parts of the cataract) and eye fluid are aspirated via the needle 16 to the collection receptacle 28 using the pumping sub-system 26. The pumping sub-system 26 may comprise one or more pumps or any suitable pump type, such as peristaltic pumps, vane pumps, or any suitable combination thereof. The phacoemulsification probe 12 is described in more detail with reference to FIG. 3.

The phacoemulsification apparatus 10 includes a signal generator 30, which is coupled with the piezoelectric actuator 22, and is configured to generate (block 104) a drive signal to drive a vibration of the piezoelectric actuator 22. In some exemplary embodiments, the signal generator 30 includes a direct digital synthesizer (DDS) 32 and a class AB amplifier 34 which are coupled together. The class AB amplifier 34 is coupled to the piezoelectric actuator 22. The DDS 32 is configured to generate the drive signal. The class AB amplifier 34 is configured to amplify the drive signal to power the piezoelectric actuator 22. The DDS 32 may be replaced by any suitable signal synthesizer. The class AB amplifier 34 may be replaced by any suitable signal amplifier, for example, but not limited to a class D amplifier.

The phacoemulsification apparatus 10 includes phase detection circuitry 36 which is configured to measure (block 106) a phase difference between: a voltage across the piezoelectric actuator 22; and a current flowing through the piezoelectric actuator 22 in response to the drive signal.

In some exemplary embodiments, the phase detection circuitry 36 may include respective analog-to-digital converters (not shown) which sample the voltage across, and the current through, the piezoelectric actuator 22, with the output of the analog-to-digital converters being digitally analyzed (e.g., by a suitable controller or processor) to compute the phase difference. Using the analog-to-digital converters is limited as described above in the overview section.

In some exemplary embodiments, the phase detection circuitry 36 uses analog multipliers as described in more detail with reference to FIGS. 4 and 5.

The phacoemulsification apparatus 10 includes a micro-controller 38. The micro-controller 38 may be replaced by any suitable controller or processor to perform the functions of the micro-controller 38 as described herein. In practice, some or all of the functions of the micro-controller 38 may be combined in a single physical component or, alternatively, implemented using multiple physical components. These physical components may comprise hard-wired or programmable devices, or a combination of the two. In some embodiments, at least some of the functions of the micro-controller 38 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The micro-controller 38 may receive user-based commands via a user interface 40, which may include setting a vibration mode and/or frequency of the piezoelectric actuator 22, adjusting the vibration mode and/or frequency of the piezoelectric actuator 22, setting or adjusting a stroke amplitude of the needle 16, setting or adjusting an irrigation and/or aspiration rate of the pumping sub-system 26. The micro-controller 38 is configured to control the pumping sub-system 26 and the signal generator 30 based on the user-based commands. The user interface 40 may include any suitable user interface devices, for example, but not limited to any one or more of the following: a keyboard, a keypad, a touch screen, or a pointing device (such as a mouse, stylus, or joystick).

The micro-controller 38 is configured to adjust (block 108) the frequency of the drive signal so as to minimize the measured phase difference, whereby the piezoelectric actuator vibrates at the resonant frequency. It should be noted that the term "vibrating at the resonant frequency," in all grammatical forms thereof, is defined as approximately vibrating at the resonant frequency, due to noise, thermal effects and bandwidth limitations, for example. The micro-controller 38 may adjust the frequency of the drive signal to minimize the measured phase difference using any suitable method, for example, based on an optimization algorithm, for example, but not limited to, including a gradient descent algorithm. An exemplary optimization method for use in the phacoemulsification apparatus 10 is described with reference to FIG. 6.

In some exemplary embodiments the piezoelectric actuator 22 may include a single resonance mode, for example, a longitudinal resonance mode (indicated using arrow 42), or a transverse resonance mode (indicated using arrow 44), or a torsion resonance mode (indicated using arrow 46). In some exemplary embodiments, the piezoelectric actuator 22 may include two (or more) different resonance modes having two (or more) respective resonant frequencies. The resonance modes may include any suitable resonance modes, for example, any two or more of the following: the longitudinal resonance mode (indicated using arrow 42), or the transverse resonance mode (indicated using arrow 44), or the torsion resonance mode (indicated using arrow 46). In these exemplary embodiments, the micro-controller 38 may be configured to adjust the frequency of the drive signal so as to minimize the measured phase difference, whereby the piezoelectric actuator 22 vibrates at the resonant frequency of the user selected resonance mode.

The needle 16 shown in FIG. 1 is a straight needle. Any suitable needle may be used with the phacoemulsification probe 12, for example, a curved or bent tip needle commercially available from Johnson & Johnson Vision, Jacksonville, Fla., USA.

Figure 3:
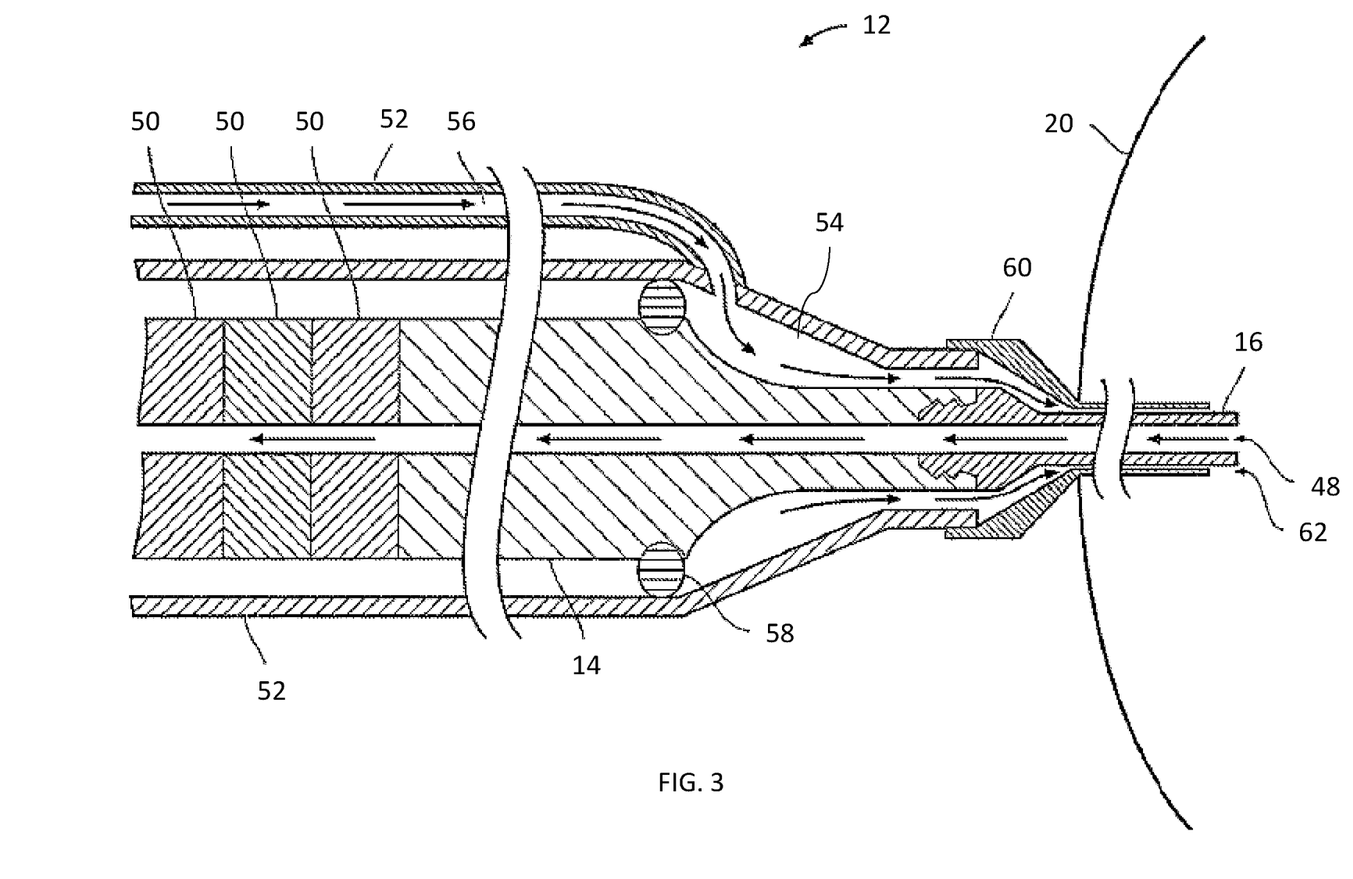
FIG. 3 is a schematic view of a phacoemulsification probe for use in the apparatus of FIG. 1 in accordance with an exemplary embodiment of the present invention.

Reference is now made to FIG. 3, which is a cross-sectional view of the phacoemulsification probe 12 for use in the apparatus 10 of FIG. 1. Generally, the phacoemulsification probe 12 includes the needle 16, defining a lumen that is operatively coupled to the collection receptacle 28 (FIG. 1) via the pumping sub-system 26 (FIG. 1) forming an aspiration line 48. The proximal end of the needle 16 is coupled to the horn 14, which has its proximal end coupled to a set of piezoelectric crystals 50 of the piezoelectric actuator 22 (FIG. 1), shown as three rings. The horn 14, crystals 50, and a proximal portion of the needle 16 are enclosed within a handpiece casing 52 having an irrigation port coupled to an irrigation line 54 defining an irrigation pathway 56. The irrigation line 54 is coupled to the irrigation reservoir 24 (FIG. 1). The horn 14 is typically an integrated metal structure, formed from any suitable metal, such as titanium, and often includes a rubber O ring 58 around the mid-section, just before the horn 14 tapers to fit with the needle 16 at the horn's 14 distal end. The O ring 58 snugly fits between the horn 14 and the casing 52. The O ring 58 seals the proximal portion of the horn 14 from the irrigation pathway 56. Thus, there is a channel of air defined between the horn 14 and the casing 52. Descriptions of handpieces known in the art are provided in U.S. Pat. No. 6,852,092 to Kadziauskas, et al., and U.S. Pat. No. 5,843,109 to Mehta, et al., by way of example.

The exemplary embodiment of the phacoemulsification probe 12 described with reference to FIG. 3 is described by way of example only. Any suitable phacoemulsification probe may be used instead of the phacoemulsification probe 12.

In preparation for the phacoemulsification procedure, a sleeve 60 is typically added to the distal end of the phacoemulsification probe 12, covering the proximal portion of the needle 16 (thus, exposing the distal tip of the needle 16), and the distal end of the irrigation pathway 56, thereby extending the pathway 56 and defining an irrigation port 62 just before the distal tip of the needle 16. The needle 16 and a portion of the sleeve 60 are then inserted through the cornea of the eye 20 to reach the lens capsule 18 (FIG. 1).

During the phacoemulsification procedure, the irrigation pathway 56, the eye's chamber and the aspiration line 48 form a fluidic circuit, where irrigation fluid enters the eye's chamber via the irrigation pathway 56, and is then aspirated through the aspiration line 48 along with other materials that the surgeon desires to aspirate out, such as the cataract. If, however, the materials, such as the cataract, are too hard and/or large to be aspirated through the aspiration line 48, the distal end of the needle 16 is ultrasonically vibrated and applied to the material to be emulsified into a size and state that can be successfully aspirated.

The needle 16 is ultrasonically vibrated by applying electric power to the piezoelectric crystals 50, which in turn, cause the horn 14 to ultrasonically vibrate, which in turn, ultrasonically vibrates the needle 16. The electric power is defined by a number of parameters, such as signal frequency and amplitude, and if the power is applied in pulses, then the parameters can further include pulse width, shape, size, duty cycle, amplitude, and so on. These parameters are controlled by the micro-controller 38 (FIG. 1) and example control of these parameters is described in U.S. Pat. No. 7,169,123 to Kadziauskas, et al.

Figure 4:
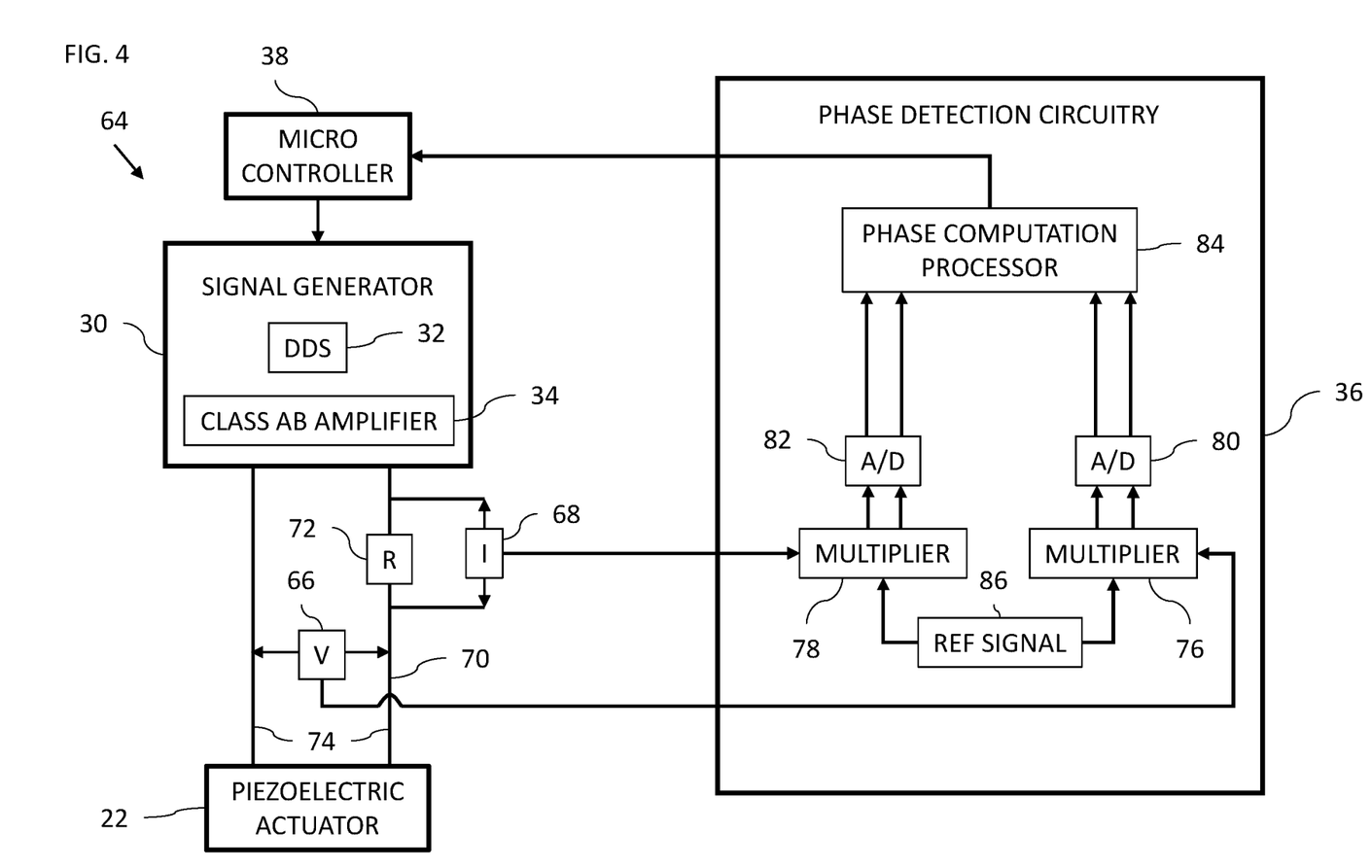
FIG. 4 is a schematic view of control elements in the apparatus of FIG. 1 in accordance with an exemplary embodiment of the present invention.
Figure 5:
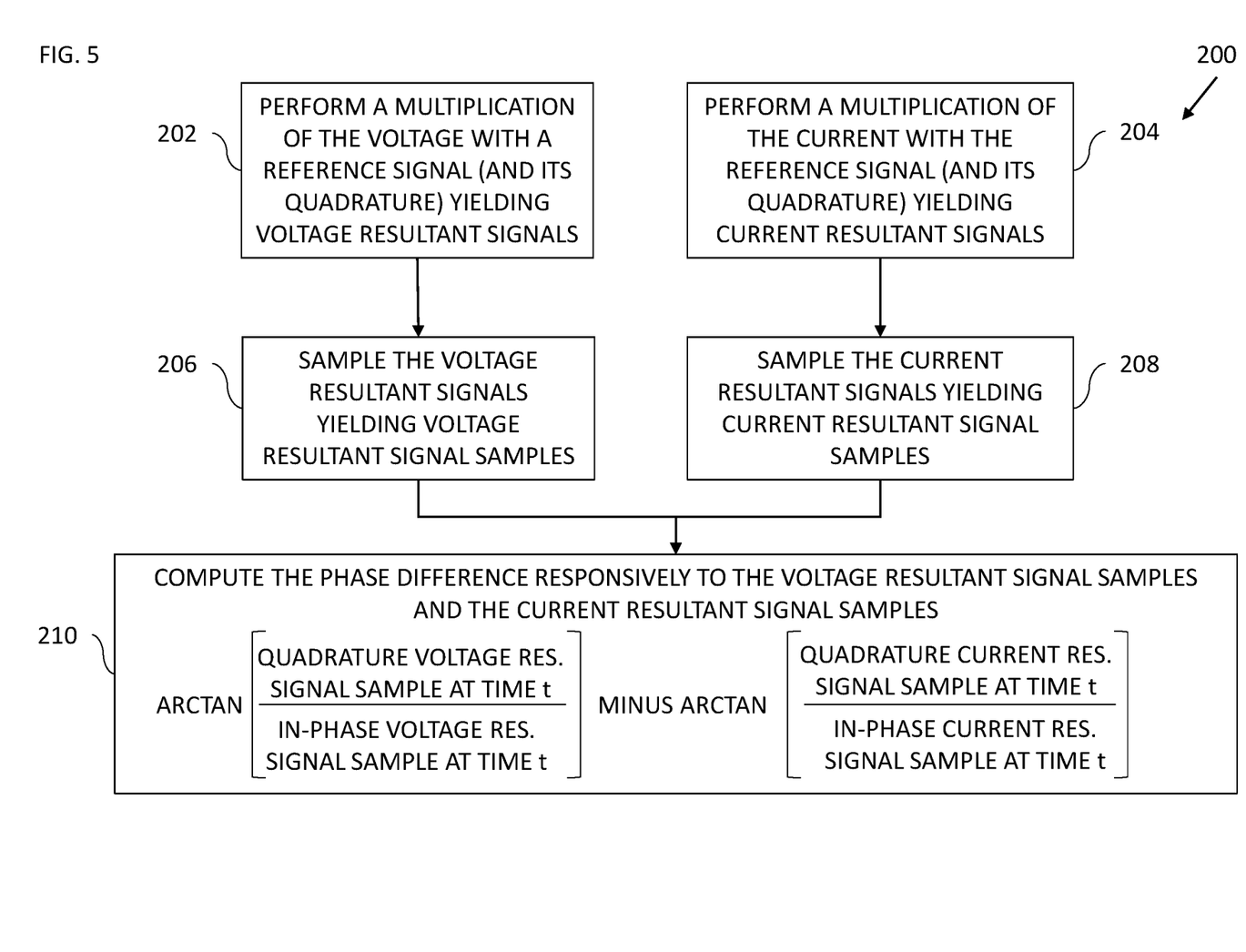
FIG. 5 is a flowchart including steps in a method of operation of the phase detection circuitry of FIG. 4 in accordance with an exemplary embodiment of the present invention.

Reference is now made to FIG. 4, which is a schematic view of control elements 64 in the apparatus 10 of FIG. 1. Reference is also made to FIG. 5, which is a flowchart 200 including steps in a method of operation of the phase detection circuitry 36 of FIG. 4.

FIG. 4 shows the micro-controller 38 coupled to the signal generator 30 to command the DDS 32 regarding the frequency of the drive signal and to receive phase data from the phase detection circuitry 36. The class AB amplifier 34 is coupled to the DDS 32 and receives the drive signal from the DDS 32 for amplification to power the piezoelectric actuator 22.

A voltage (signal) 66 across the piezoelectric actuator 22 is sourced from two connections 74 of the piezoelectric actuator 22 for processing by the phase detection circuitry 36. A current (signal) 68 flowing through the piezoelectric actuator 22 is captured for processing by the phase detection circuitry 36. The phacoemulsification apparatus 10 includes a connection 70 in series with the piezoelectric actuator 22, and a resister 72 disposed in the connection 70. The current 68 flowing through the resister 72 represents the current flowing through the piezoelectric actuator 22. The current (signal) 68 is sourced from connections either side of the resister 72.

The phase detection circuitry 36 includes an analog multiplier 76, an analog multiplier 78, an analog-to-digital convertor 80, an analog-to-digital convertor 82, and phase computation processor 84. The analog multiplier 76 has inputs across the piezoelectric actuator 22 from the connections 74. The analog multiplier 78 has inputs connected across the resister 72. Each analog multiplier 76, 78 may include circuitry for performing two independent multiplications, one based on a given reference signal 86, and one based on a quadrature reference signal, which is in quadrature (e.g., 90 degrees out-of-phase) with the given reference signal 86, which is also called the in-phase reference signal 86, described in more detail below.

The analog-to-digital convertor 80 and the analog-to-digital convertor 82 are dual channel analog-to-digital convertors. In some exemplary embodiments, the analog-to-digital convertor 80 and the analog-to-digital convertor 82 may be replaced by a four-channel analog-to-digital convertor or four single channel analog-to-digital convertors, or any suitable combination of analog-to-digital convertors.

The analog multiplier 76 is configured to perform (block 202) a multiplication of the voltage 66 with the in-phase reference signal 86 and a multiplication of the voltage 66 with the quadrature reference signal yielding two respective DC voltage resultant signals, an in-phase voltage resultant signal (based on the in-phase reference signal 86) and a quadrature voltage resultant signal (based on the quadrature reference signal). At any time, t, the arctan of: the amplitude of the quadrature voltage resultant signal divided by; the amplitude of the in-phase voltage resultant signal, is proportional to the phase difference between the voltage signal 66 and the reference signal 86. In some embodiments, the reference signal includes the drive signal. The analog multiplier 78 is configured to perform (block 204) a multiplication of the current 68 with the in-phase reference signal 86 and the quadrature reference signal yielding two respective DC current resultant signals, an in-phase current resultant signal (based on the in-phase reference signal 86) and a quadrature current resultant signal (based on the quadrature reference signal). At any time, t, the arctan of: the amplitude of the quadrature current resultant signal divided by; the amplitude of the in-phase current resultant signal, is proportional to the phase difference between the current signal 68 and the reference signal 86. The steps of blocks 202 and 204 are generally performed continuously while the piezoelectric actuator 22 is being powered. Some commonly available analog multiplier integrated circuits (ICs) are MPY634 from Texas Instruments, AD534, AD632 and AD734 from Analog Devices.

The analog-to-digital convertor 80 is configured to respectively sample (block 206) the two voltage resultant signals yielding respective voltage resultant signal samples (e.g., multiple in-phase voltage resultant signal samples and multiple quadrature voltage resultant signal samples). The analog-to-digital convertor 82 is configured to respectively sample (block 208) the two current resultant signals yielding respective current resultant signal samples (e.g., multiple in-phase current resultant signal samples and multiple quadrature current resultant signal samples). The sampling frequency and phase of the analog-to-digital convertors 80, 82 are generally synchronized so that they sample the signals at the same time. The sampling frequency may be any suitable frequency, for example, 500 kHz (or less), 1000 kHz, 2000 kHz (or more).

The phase computation processor 84 (illustrated in FIG. 4) is configured to compute (block 210) respective phase differences (between the voltage 66 and the current 68 at different times) responsively to the respective voltage resultant signal samples and the respective current resultant signal samples. For example, the phase computation processor 84 is configured to compute the phase difference between the voltage 66 across the piezoelectric actuator 22 and the reference signal 86 at time t by computing a first arctan of: (a) the quadrature voltage resultant signal sample at time t divided by; (b) the in-phase voltage resultant signal sample at time t. Similarly, the phase computation processor 84 is configured to compute the phase difference between the current 68 flowing through the piezoelectric actuator 22 and the reference signal 86 at time t by computing second arctan of: (a) the quadrature current resultant signal sample at time t divided by; (b) the in-phase current resultant signal sample at time t. The phase computation processor 84 is configured to compute the phase difference between the voltage signal 66 and the current signal 68 at time t, by subtracting the results of the first and second arctan from each other.

Figure 7:
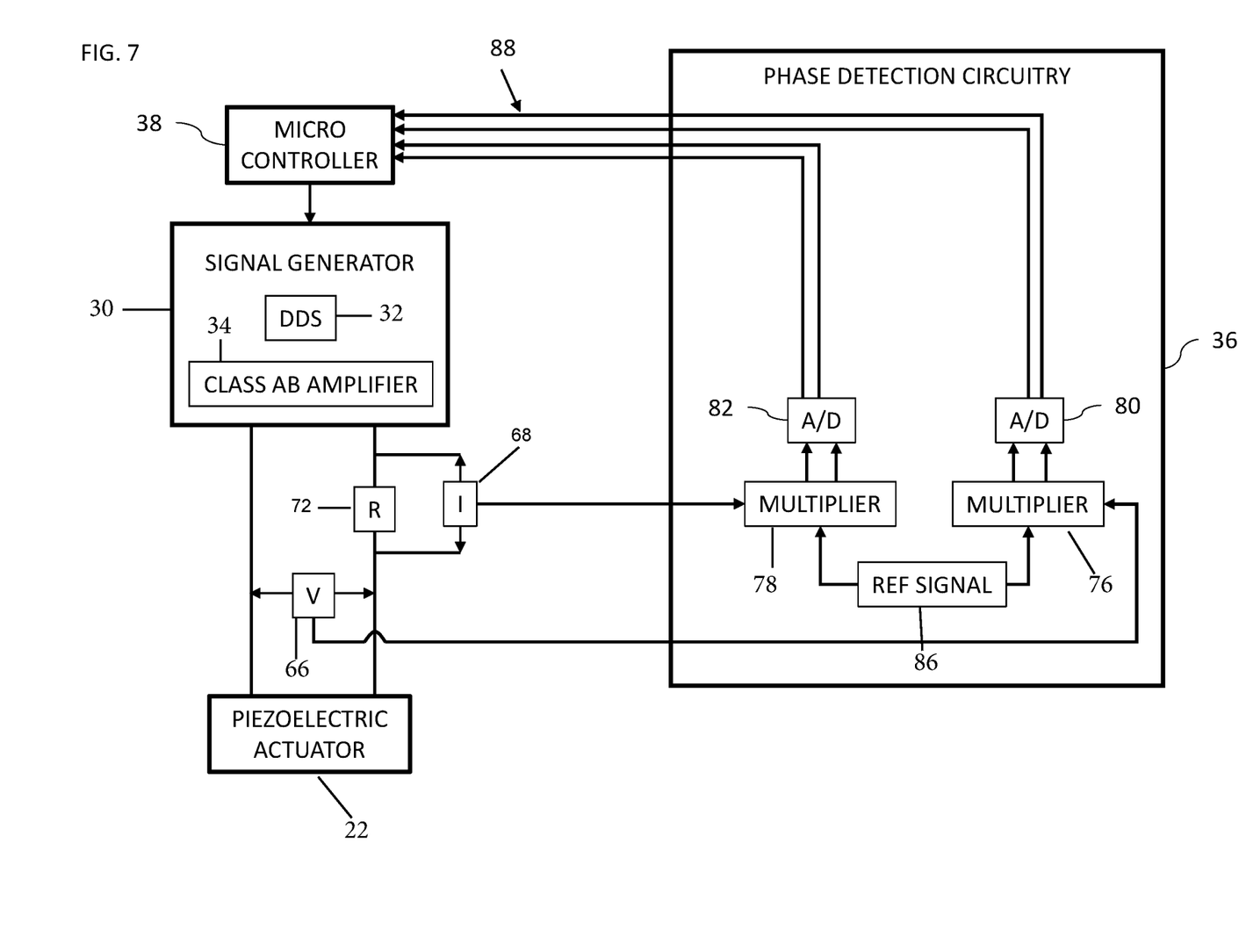
FIG. 7 is schematic view of alternative control elements in the apparatus of FIG. 1 in accordance with an exemplary embodiment of the present invention.

The phase computation processor 84 may form part of the functionality of: the micro-controller 38 as shown in FIG. 7 (and not part of the phase detection circuitry 36); or a dedicated microcontroller. In practice, some or all of the functions of the phase computation processor 84 may be combined in a single physical component (e.g., the micro-controller 38) or, alternatively, implemented using multiple physical components. These physical components may comprise hard-wired or programmable devices, or a combination of the two. In some embodiments, at least some of the functions of the phase computation processor 84 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

Figure 6:
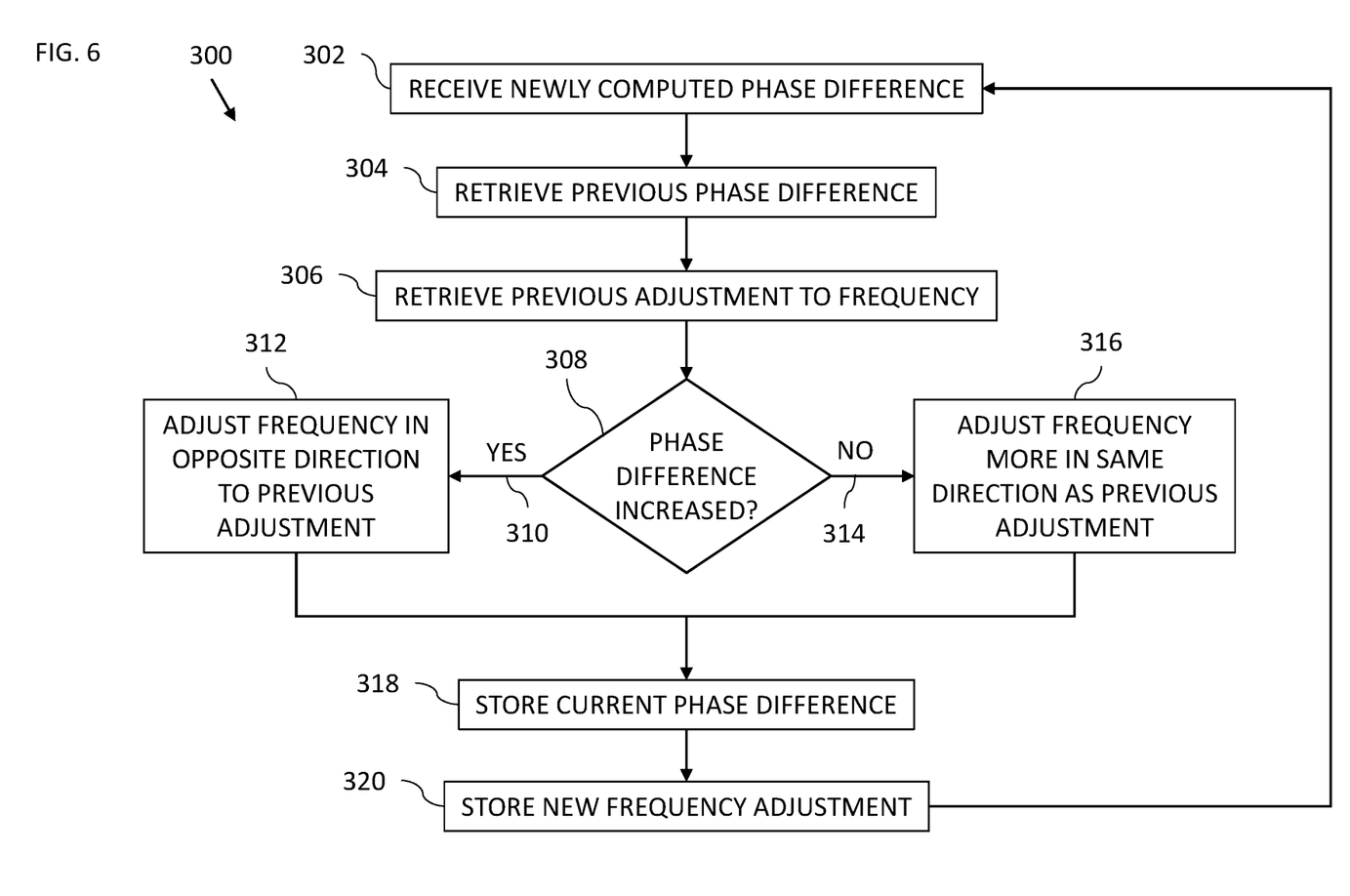
FIG. 6 is a flowchart including steps in a method of operation of the microcontroller of FIG. 4 in accordance with an exemplary embodiment of the present invention.

Reference is now made to FIG. 6, which is a flowchart 300 including steps in a method of operation of the micro-controller 38 of FIG. 4.

The micro-controller 38 (FIG. 4) is configured to receive (block 302) a newly computed phase difference from the phase computation processor 84 (FIG. 4), which in some exemplary embodiments may be incorporated into the functionality of the micro-controller 38.

The micro-controller 38 is configured to retrieve (block 304) a previous phase difference (i.e., the phase difference received prior to the newly computed phase difference) and to retrieve (block 306) a previous adjustment to the drive frequency (i.e., computed based on the previous phase difference).

The micro-controller 38 is configured to compare the newly computed phase difference with the previous phase difference to determine whether the newly computed phase difference represents an increase over the previous phase difference in a step of decision block 308.

If the newly computed phase difference represents an increase over the previous phase difference (branch 310), the micro-controller 38 is configured to adjust (block 312) the drive frequency in an opposite direction to the previous adjustment. For example, if the previous adjustment increased the drive frequency, the current adjustment will be to decrease the drive frequency, and vice-versa. If the newly computed phase difference represents a decrease over the previous phase difference (branch 314), the micro-controller 38 is configured to adjust (block 316) the drive frequency more in the same direction as the previous adjustment. The adjustment to the frequency may be proportional to the phase difference or the adjustment may be a fixed value.

The micro-controller 38 is configured to store (block 318) the current phase difference (i.e., the newly computed phase difference) and to store (block 320) the new frequency adjustment.

The steps of the flowcharts 100, 200, and 300 described herein may be performed in any suitable order with some of the steps optionally being performed simultaneously where possible.

Reference is now made to FIG. 7, which is schematic view of alternative control elements 88 in the apparatus 10 of FIG. 1. The control elements 88 are substantially the same as the control elements 64 of FIG. 4 except that the control elements 88 do not include the phase computation processor 84 in the phase detection circuitry 36. The functionality of the phase computation processor 84 is included in the micro-controller 38. The outputs of the analog-to-digital convertor 80 and the analog-to-digital convertor 82 are connected to the micro-controller 38 which processes the respective voltage resultant signal samples and the respective current resultant signal samples to compute the respective phase differences.

Figure 8:
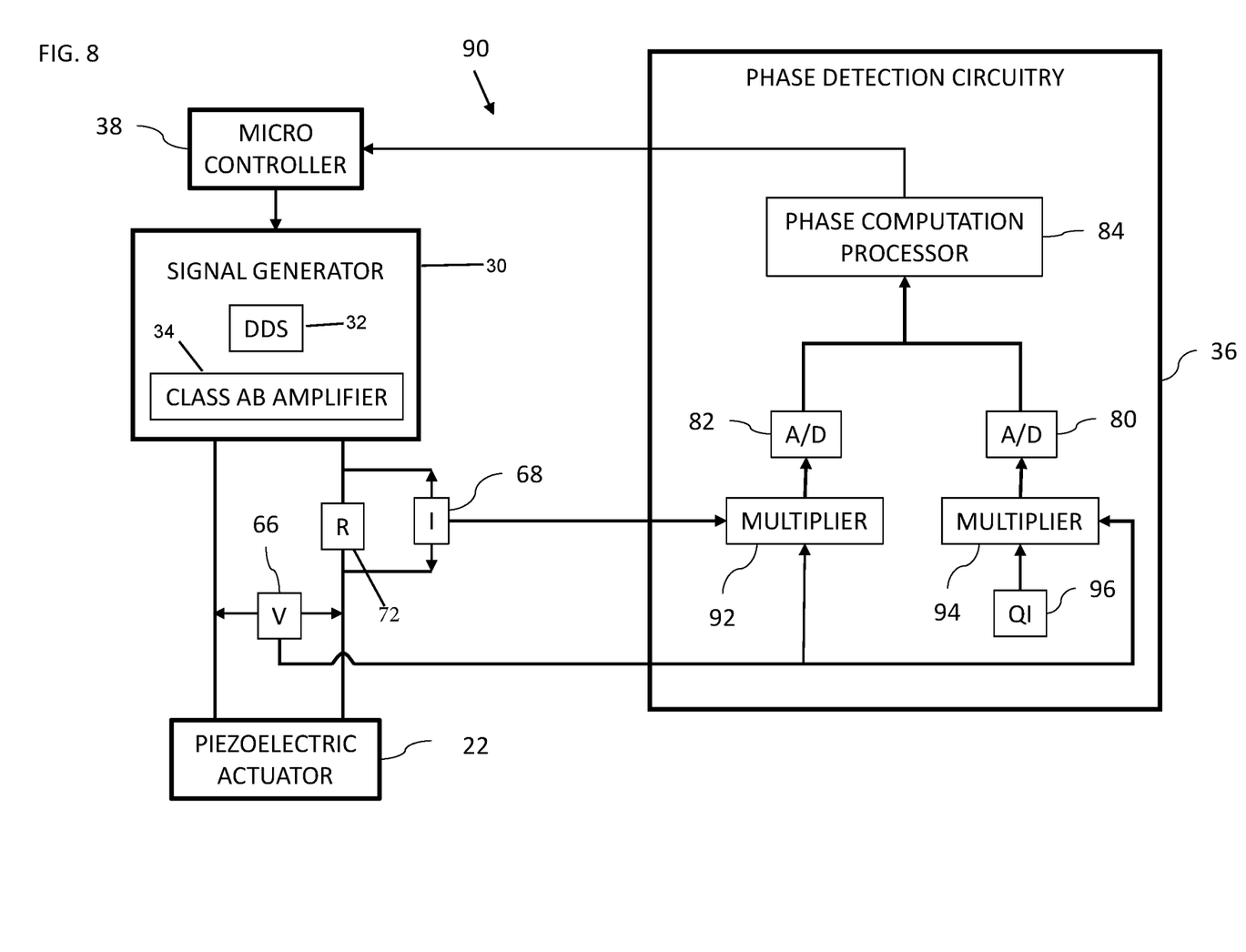
FIG. 8 is schematic view of second alternative control elements in the apparatus of FIG. 1 in accordance with an exemplary embodiment of the present invention.

Reference is now made to FIG. 8, which is schematic view of second alternative control elements 90 in the apparatus 10 of FIG. 1. In some embodiments, respective analog multipliers 92, 94 are configured to perform a multiplication of the voltage 66 with the current 68, and a multiplication of the voltage 66 with a signal 96 which is in quadrature with the current 68 yielding two respective DC resultant signals, an in-phase resultant signal (based on the current signal 68) and a quadrature resultant signal (based on the signal 96 which is in quadrature with the current signal 68). At any time, t, the arctan of: the amplitude of the quadrature resultant signal divided by; the amplitude of the in-phase resultant signal, is proportional to the phase difference between the voltage signal 66 and the current signal 68. The respective analog-to-digital convertors 82, 80 are configured to respectively sample: the in-phase resultant signal yielding in-phase resultant signal samples; and the quadrature resultant signal yielding quadrature resultant signal samples. The phase computation processor 84 (which may be incorporated into the microcontroller 38 is configured to compute respective phase differences (between the voltage 66 and the current 68 at different times) responsively to the respective resultant signal samples. For example, the phase computation processor 84 is configured to compute the phase difference between the voltage 66 across the piezoelectric actuator 22 and the reference signal 86 at time t by computing an arctan of: (a) the quadrature resultant signal sample at time t, divided by; (b) the in-phase resultant signal sample at time t.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A phacoemulsification apparatus comprising:
   a phacoemulsification probe including: a horn; a needle mounted in the horn and configured for insertion into a lens capsule of a human eye; and a piezoelectric actuator configured to vibrate the horn and the needle and having a resonant frequency;
   a signal generator configured to generate a drive signal to drive a vibration of the piezoelectric actuator;
   phase detection circuitry configured to measure a phase difference between: a voltage across the piezoelectric actuator; and a current flowing through the piezoelectric actuator in response to the drive signal, wherein the phase detection circuitry includes:
      a first analog multiplier configured to perform a multiplication of the voltage with a reference signal yielding voltage resultant signals; and
      a second analog multiplier configured to perform a multiplication of the current with the reference signal yielding current resultant signals; and
   a controller configured to adjust a frequency of the drive signal so as to minimize the measured phase difference, whereby the piezoelectric actuator vibrates at the resonant frequency.

2. The apparatus according to claim 1, wherein the phase detection circuitry also includes:
   a first analog-to-digital convertor configured to sample the voltage resultant signals yielding voltage resultant signal samples;
   a second analog-to-digital convertor configured to sample the current resultant signals yielding current resultant signal samples; and
   a phase computation processor configured to compute the phase difference responsively to the voltage resultant signal samples and the current resultant signal samples.

3. The apparatus according to claim 1, further comprising: a connection in series with the piezoelectric actuator; and a resister disposed in the connection, wherein the second analog multiplier has inputs connected across the resister.

4. The apparatus according to claim 1, wherein the reference signal includes the drive signal.

5. The apparatus according to claim 1, wherein the phase detection circuitry includes:
   analog multipliers configured to perform a multiplication of the voltage with the current yielding resultant signals;
   analog-to-digital convertors configured to sample the resultant signals yielding resultant signal samples; and
   a phase computation processor configured to compute the phase difference responsively to the resultant signal samples.

6. The apparatus according to claim 1, wherein the controller is configured to adjust the frequency of the drive signal so as to minimize the measured phase difference based on an optimization algorithm.

7. The apparatus according to claim 6, wherein the optimization algorithm includes a gradient descent algorithm.

8. The apparatus according to claim 1, wherein the signal generator includes a direct digital synthesizer (DDS) and a class AB amplifier, the DDS being configured to generate the drive signal, the class AB amplifier being configured to amplify the drive signal to power the piezoelectric actuator.

9. The apparatus according to claim 1, wherein the piezoelectric actuator includes two different resonance modes having two respective resonant frequencies, the controller being configured to adjust the frequency of the drive signal so as to minimize the measured phase difference, whereby the piezoelectric actuator vibrates at a respective one of the resonant frequencies of a respective selected one of the resonance modes.

10. The apparatus according to claim 9, wherein the resonance modes include a longitudinal resonance mode and a transverse or torsion resonance mode.

11. A phacoemulsification method comprising:
   inserting a needle of a phacoemulsification probe into a lens capsule of a human eye, the probe also including a horn in which the needle is mounted;
   generating a drive signal to drive a vibration of a piezoelectric actuator having a resonant frequency, the piezoelectric actuator vibrating the horn and the needle;
   measuring a phase difference between: a voltage across the piezoelectric actuator; and a current flowing through the piezoelectric actuator in response to the drive signal, wherein the measuring of the phase difference includes performing a multiplication of the voltage with a reference signal yielding voltage resultant signals; and performing a multiplication of the current with the reference signal yielding current resultant signals; and
   adjusting a frequency of the drive signal so as to minimize the measured phase difference, whereby the piezoelectric actuator vibrates at the resonant frequency.

12. The method according to claim 11, further comprising:
  sampling the voltage resultant signals yielding voltage resultant signal samples;
  sampling the current resultant signals yielding current resultant signal samples; and
  computing the phase difference responsively to the voltage resultant signal samples and the current resultant signal samples.

13. The method according to claim 11, wherein the reference signal includes the drive signal.

14. The method according to claim 11 further comprising:
  performing a multiplication of the voltage with the current yielding resultant signals;
  sampling the resultant signals yielding resultant signal samples; and
  computing the phase difference responsively to the resultant signal samples.

15. The method according to claim 11, wherein the adjusting includes adjusting the frequency of the drive signal so as to minimize the measured phase difference based on an optimization algorithm.

16. The method according to claim 15, wherein the optimization algorithm includes a gradient descent algorithm.

17. The method according to claim 11, further comprising amplifying the drive signal to power the piezoelectric actuator.

18. The method according to claim 11, wherein the piezoelectric actuator includes two different resonance modes having two respective resonant frequencies, wherein the adjusting includes adjusting the frequency of the drive signal so as to minimize the measured phase difference, whereby the piezoelectric actuator vibrates at a respective one of the resonant frequencies of a respective selected one of the resonance modes.

19. The method according to claim 18, wherein the resonance modes include a longitudinal resonance mode and a transverse or torsion resonance mode.

* * * * *